United States Patent [19]
Roth et al.

[11] Patent Number: 5,357,799
[45] Date of Patent: Oct. 25, 1994

[54] METHOD AND APPARATUS FOR DETERMINING ABRASION POTENTIAL OF TIRE TREADS

[75] Inventors: Vladimir Roth; John L. Turner, both of Akron; Stephen M. Vossberg, Uniontown, all of Ohio

[73] Assignee: Bridgestone Corporation, Tokyo, Japan

[21] Appl. No.: 913,573

[22] Filed: Jul. 14, 1992

[51] Int. Cl.$^5$ ............................................. G01M 17/02
[52] U.S. Cl. ........................................... 73/146; 73/8; 356/71
[58] Field of Search ............................ 73/146, 7, 8, 9; 128/779; 356/71, 35; 358/106

[56] References Cited

U.S. PATENT DOCUMENTS

| | | | |
|---|---|---|---|
| 3,966,326 | 6/1976 | Brull et al. | 356/114 |
| 4,095,464 | 6/1978 | Breedijk | 73/146 |
| 4,858,621 | 8/1989 | Franks | 128/779 |
| 4,986,118 | 1/1991 | Pottinger | 73/146 |
| 5,088,321 | 2/1992 | Kajikawa et al. | 73/146 |
| 5,092,166 | 3/1992 | Wada et al. | 73/146 |
| 5,174,151 | 12/1992 | Adachi et al. | 73/146 |

FOREIGN PATENT DOCUMENTS

| | | | |
|---|---|---|---|
| 0426457 | 8/1991 | European Pat. Off. | 73/146 |
| 4126754 | 2/1992 | Fed. Rep. of Germany | 73/146 |
| 4126772 | 2/1992 | Fed. Rep. of Germany | 73/146 |
| 0894414 | 12/1981 | U.S.S.R. | 73/8 |
| 1307278 | 4/1987 | U.S.S.R. | 73/146 |

OTHER PUBLICATIONS

"Contact Stresses As Predicators of Tread Wear," by W. K. Shepherd, 1986.
Journal of Medical Engineering & Technology, May 3, 1980, pp. 136–142.
Mechanics of Pneumatic Tires; Editor Samuel K. Clark; U.S. DOT.
"An Experimental Very High Resolution Tactile Sensor Array," by Mott, Lee, and Nicholls.

*Primary Examiner*—Donald Woodiel
*Assistant Examiner*—Richard A. Moller
*Attorney, Agent, or Firm*—David A. Thomas

[57] ABSTRACT

An apparatus and technique for determining the abrasion potential for tire treads is presented. A tire is rotatably and forcefully brought into contacting engagement with a reflective surface received upon an illuminated glass plate. A charge coupled device monitors the internal reflection light which evidences a grey level corresponding to the force of engagement between the associated portion of the tire and the glass support plate. A marker is placed upon the tire centrally within a region of interest. The video image of the marker and region of interest is analyzed as to slip and force at that area. The product of the slip and force functions is an indication of frictional work at the interface between the tire and support surface and is correspondingly an indication of the propensity of the tire to wear.

19 Claims, 4 Drawing Sheets

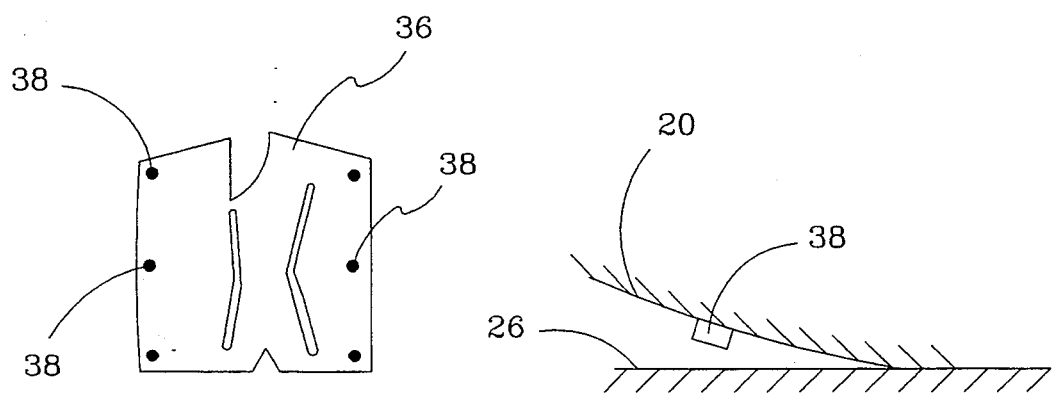
FIG. 3
FIG. 4
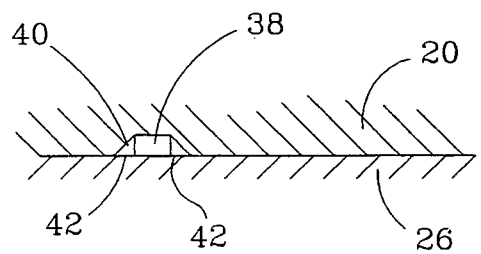
FIG. 5
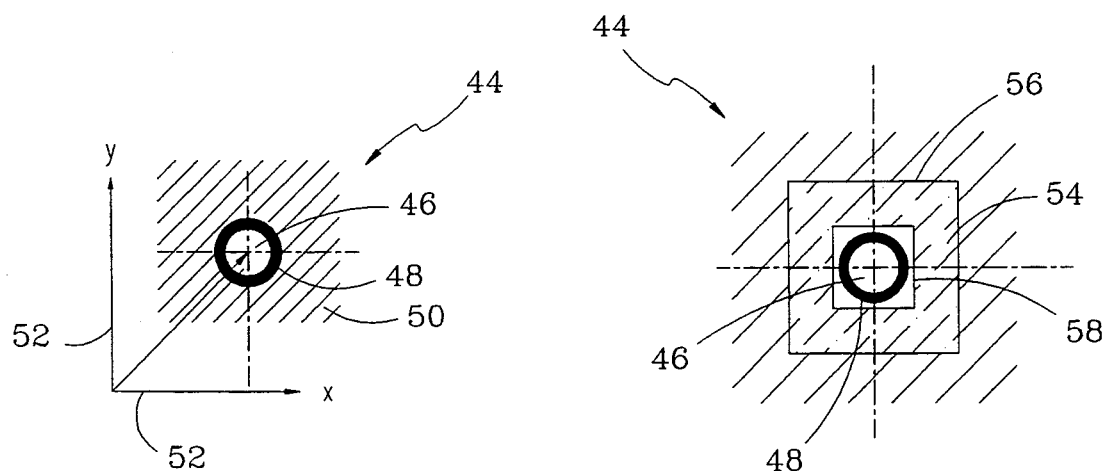
FIG. 6
FIG. 7

METHOD AND APPARATUS FOR DETERMINING ABRASION POTENTIAL OF TIRE TREADS

TECHNICAL FIELD

The invention herein resides in the art of techniques and apparatus for analyzing tire treads in determining the abrasion potential thereof. More particularly, the invention relates to such a method and apparatus for making such determinations without contacting the tire while obtaining data therefrom. Specifically, the invention pertains to a method and apparatus for simultaneously determining slippage and normal force between a support surface and a defined area on the tire tread, and assessing the propensity for wear as a function of the product of such slippage and force.

BACKGROUND ART

It is well known that tire wear is a function of the frictional work between tile tire and a supporting surface when the two are in frictional contact with each other. It is further known that tire wear at a particular location is proportional to such frictional work according to the formula W=uNs, where W=frictional work, u=coefficient friction between the tire and the support surface, N=normal force between the tire and support surface at the location of interest, and s=slip between tile tire and support surface at the location of interest. Accordingly, tire wear at a given location is a direct function of the product of N (normal force) and s (slip) at that location.

With a knowledge of the foregoing, one can analytically determine the propensity of a tire to wear by measuring N and s. Known prior systems have measured N and sought to calculate s, but have been generally incapable of simultaneously measuring or determining both at a given point on a tire. In general, the prior art has employed mechanical force transducers for determining the force upon the tire at an area of interface with a support surface, but such techniques and apparatus have not been given to a simultaneous determination of slip at the interface. Using such techniques and apparatus, it has been found that the slip of interest removed the area of concern from contact with the pressure transducer such that the force and slip measurements were taken from two distinctly different areas. Accordingly, the prior art has been given not only to inaccuracies in measurement, but an inability to directly correlate a determined normal force with a determined slip function. Consequently, the product Ns, intended to be proportional to frictional work and propensity for wear, is generally inaccurate and incapable of providing a reliable assessment.

There is a need in the art for a noncontact measuring or monitoring system to simultaneously and accurately obtain both slip (s) and force (N) measurements at specified locations on a tire, which measurements may then be employed to determine the propensity of wear of the tire at that specific location. There is a most important need in the art for the ability to take such simultaneous measurements to assure that the data employed to determine wear propensity are taken from the same area of the tire under the same conditions.

It has been known in the art that tire contact stresses may be employed as indicators of tread wear. Such general recognition has been pronounced in "Contact Stresses As Predictors Of Tread Wear," by W. K. Shepherd, copyright 1986 by Michelin Americas Research & Development Corp. and in "Mechanics of Pneumatic Tires," edited by Samuel K. Clark, and published by the U.S. Department of Transportation in 1981. Additionally, it has been known that force measurements may be taken from the light reflected from an illuminated plate of glass when an article is brought into forceful contacting engagement with a reflective shield received upon the plate of glass. This concept of measuring force or pressure upon a surface by the measurement of internal reflection light (IRL) is generally known and is taught in U.S. Pat. No. 4,858,621. However, the prior art has failed to teach an apparatus or technique for employing IRL as a means for determining a propensity for tread wear. More particularly, the prier art has failed to teach any such apparatus or technique whereby force and slip measurements of a tire and support surface interface could be simultaneously measured and employed for determining a propensity for tread wear.

DISCLOSURE OF INVENTION

In light of the foregoing, it is a first aspect of the invention to provide an apparatus and technique for determining abrasion potential of a tire tread which is capable of obtaining simultaneous measurements of normal force and slip between the tire and a support surface.

Another aspect of the invention is the provision of an apparatus and technique for determining abrasion potential of a tire tread which measures the normal force and slip between a tire and its support surface without contacting either the tire or the support surface.

A further aspect of the invention is the provision of an apparatus and technique for determining abrasion potential of a tire tread in which force and slippage are measured over the same area of the tread irrespective of the magnitude of the slippage.

Yet an additional aspect of the invention is the provision of an apparatus and technique for determining abrasion potential of a tire tread which employs measurement techniques which do not appreciably impact the force and/or slip characteristics of the tire and support surface interface.

Still an additional aspect of the invention is the provision of an apparatus and technique for determining abrasion potential of a tire tread which obviates the need of mechanical force or pressure transducers.

Still another aspect of the invention is the provision of an apparatus and technique for determining abrasion potential of a tire tread which is highly reliable in implementation and characterized by high resolution in data acquisition, while readily conducive to construction and use by employing; state of the art apparatus and techniques.

The foregoing and other aspects of the invention which will become apparent as the detailed description proceeds are achieved by apparatus for determining abrasion potential for tire treads, comprising: a glass plate; a source of illumination adjacent and illuminating said glass plate; first means for effecting forceful rolling engagement of a tire upon said glass plate; second means for viewing a contact interface between said tire and said glass plate, and generating a digitized video image of a selected area thereof; and third means in operative communication with said second means for receiving said digitized video image, and determining therefrom a force of interengagement and an amount of slip between said selected area and said glass plate and an abrasion potential for said selected area as a function of said force and said slip.

Other aspect of the invention which will become apparent herein are achieved by a method for determining abrasion potential for tire treads, comprising: placing a marker upon a tire at an area of interest; rolling said tire upon an illuminated glass plate; obtaining a digitized video image of an area of interengagement between said tire and said glass plate; locating said marker within said video image and defining a region of interest about said marker; monitoring slip of said marker in said area of interengagement; determining a force of interengagement between said tire and said glass plate in said region of interest; and assessing an abrasion potential for said tire at said region of interest as a function of said force and slip.

DESCRIPTION OF DRAWINGS

For a complete understanding of the objects, techniques, and structure of the invention reference should be made to the following detailed description and accompanying drawings wherein:

FIG. 3 is a top plan view of a tire lug on a tread portion of interest having tags or markers thereon;

FIG. 4 is an illustrative side view of a tire having a marker thereof, the tire being received upon a support surface;

FIG. 5 is an illustrative side view of the tire upon the support surface of FIG. 4, with the marker being in contact with the support surface;

FIG. 6 is an illustrative plan view of the marker area on the tire in contact with the support surface as viewed by a charge coupled device as in FIGS. 1 and 2;

FIG. 7 is an illustrative plan view of the marker area of FIG. 6 showing the region of interest of the contact interface between the tire and support surface;

BEST MODE FOR CARRYING OUT THE INVENTION

Figure 1:
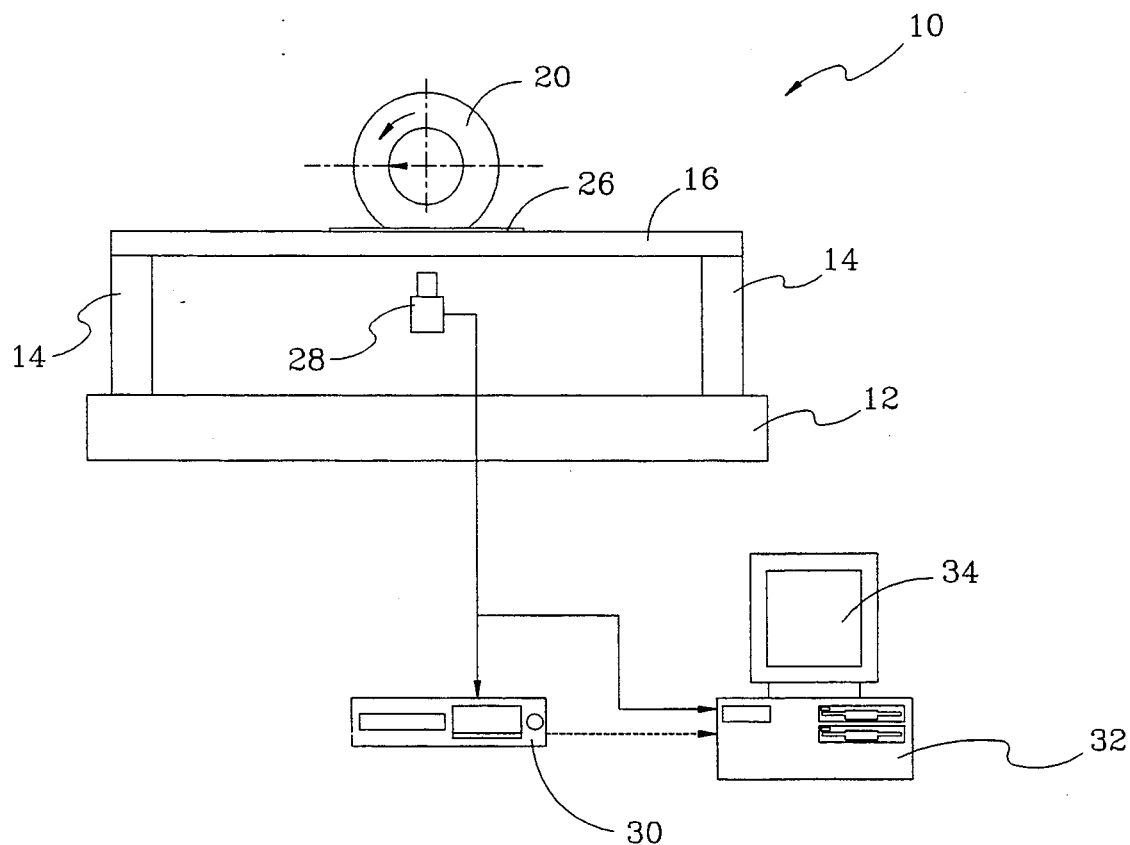
FIG. 1 is a front schematic view of a system for determining tire wear propensity according to the invention.
Figure 2:
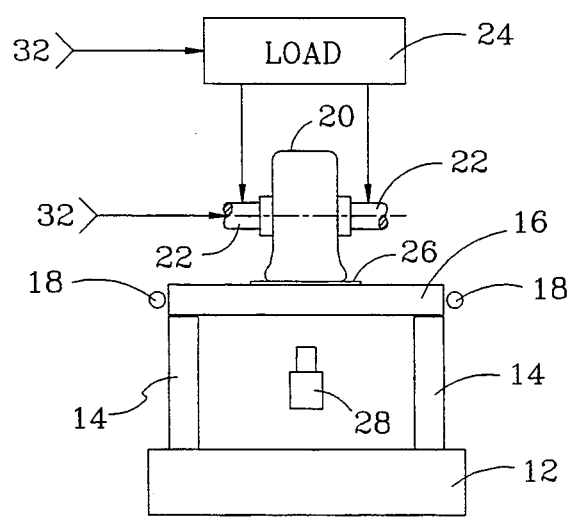
FIG. 2 is a side schematic view of the system of FIG. 1.

Referring now to the drawings and more particularly FIGS. 1 and 2, it can be seen that a system for determining the wear propensity of a tire is designated generally by the numeral 10. As shown, a support bed 12 receives a pair of end members or posts 14 at opposite ends thereof for receiving and supporting a glass plate 16. Positioned laterally along the sides of the glass plate 16, and on opposite sides thereof, are lamps or appropriate light sources 18, the function of which is to illuminate the interior of the glass plate 16 to allow for the generation of internal reflection light (IRL) for practice of the process of the invention.

A tire 20 is rotatably received upon an axle 22 which is loaded by an appropriate force generating means such as the load 24. It will be appreciated that the load 24 may be either fixed or variable. When fixed, the load 24 may comprise a fixed mass, while a variable load may be achieved by means of hydraulic or pneumatic pistons or the like. Suffice it to say that a control means is provided for loading the tire 20 against the glass plate 16 which serves as a tire support surface. Additionally, movement of the tire 20 may be achieved by any appropriate means such as by a mechanical carriage or an actual vehicle or trailer.

A reflective surface 26 is interposed between the tire 20 and glass support plate 16. The reflective surface 26 may be of any of various natures, but in a preferred embodiment simply comprises a sheet of paper having a thickness on the order of 0.002–0.01 inch. Those skilled in the art will appreciate that the reflective surface 26 provides for the generation of internal reflection light (IRL) when a force is applied to the glass plate 16 through the reflective surface 26. In the embodiment shown, the footprint of the tire 20 will be apparent through the IRL generated when the tire 20 is forcefully loaded upon the reflective support sheet 26 against the illuminated glass plate 16, as shown. The IRL is viewed by an appropriate video source such as a charge coupled device (CCD) 28, appropriate vidicon, or the like. It will be understood that the CCD 28 generates a digitized image of its field of view which, in this instance, includes at least a portion of the footprint of the tire 20 as evidenced by the IRL generated by the forceful engagement of the tire 20 upon the glass plate 16 through the reflective surface 26.

It is also contemplated as a selective feature of the invention that a video cassette recorder 30 may be interconnected with the CCD 28 to instantaneously receive and store the image obtained by the CCD 28 of the tire and support surface interface. Of course, other suitable data storage devices may also be employed to record the video image for later processing. In either event, the video image from the CCD 28 or as received and stored by the video cassette recorder 30 is fed to and received by a microprocessor 32 or other suitable control and data processing unit. The microprocessor 28 not only receives and processes data from the CCD 28 or VCR 30, but is also employed to regulate the load 24 to effect the forceful engagement of the tire 20 upon the glass support plate 16 through the reflective surface 26, and to also effect rolling motion of the tire 20 upon the glass support plate 16. A CRT or other appropriate video screen 34 is provided in communication with the microprocessor 32 to allow for presentation of data or calculations undertaken by the microprocessor 32 and/or the video image viewed by the CCD 28. Of course, the screen 34 also serves as a means of communication with an operator.

In accordance with the invention, particular areas upon the tire 20 may be marked or otherwise designated as being areas of interest for monitoring pressure and slip at the tire and support surface interface. As shown in FIG. 3, a typical tire lug 36 is provided with a plurality of tags or markers 38 thereon, each marker 38 designating a particular area of interest upon the tire lug 36. The markers 38 are suitably adhered to the tread surface of the lug 36 as by adhesive or the like. While the markers 38 may be of various configurations and structures, it is preferred that the same comprise discs having a thickness on the order of 0.005–0.010 inch, and more preferably 0.007 inch. Similarly, the marker discs 38 preferably have a diameter on the order of 0.05–0.10 inch, and more preferably on the order of 0.07–0.08 inch. It will be appreciated that the small diameter and thickness of the marker discs 38 are such that the discs 38 do not impact the force or slip characteristics of the tire 20 upon the glass support plate 16. It will further be appreciated that the diameter of the markers 38 may depend upon the resolution of the CCD 28, but it has been found that high resolution CCD devices have ample resolution to allow for reduction in size of the markers 28 to the range presented above.

As shown in FIG. 4, as the tire 20 is rotated upon the reflective surface 26, the marker 38 is brought into proximity therewith. In FIG. 5, the tire 20 is so engaged with the planar reflective surface 26 received upon the glass support plate 16, that the marker 38 is in contacting engagement therewith. As illustrated, the thickness of the marker 38, somewhat exaggerated in the drawing, causes a slight deflection of the tire 20 about the circumference thereof so as to establish a void 40 of truncated cone configuration between the tire 20 and the reflective surface 26 at the area of the marker 38. Accordingly, an area 42 of ring-like configuration is defined between the regions of contact between the marker 38 and the reflective surface 26 and the tire 20 and reflective surface 26. The ring-like non contact area 42 circumferentially encompasses the area in forceful contact with the marker 38.

FIG. 6 illustrates a view by the CCD 28 of the region of the marker 38, such view being taken from a side opposite the glass plate 16 from the tire 20. This area, designated generally by the numeral 44, is comprised of a plurality of discrete picture elements (pixels), each having a gray level corresponding to the light intensity of the associated area corresponding to the pixel within the field of view of the CCD 28. As shown in the area 44, an extremely light area 46, corresponding to the circular region of contact of the disc marker 38 with the reflective surface 26, is apparent. The value of the associated pixels in the area 46 would typically be near the white end of the spectrum, while the pixels of the dark ring 48 would be near the opposite end. Those skilled in the art will readily appreciate that the dark ring 48 corresponds to the ring-like non contact area 42 encircling the marker 38 as depicted in FIG. 5. The remaining contact area 50, corresponding to a region of contact of the tire 20 with the reflective surface 26 about the marker 38 would have a grey level value between that of the areas 46, 48 just described. The location of various features within the area 44 may be determined in a two axes coordinate system 52 established within the digitized image of the CCD 28 as established by the microprocessor 32. For example, the exact location of the center of the bright circular area 46 or surrounding dark area 48 may be readily determined in such a coordinate system.

It should now be readily apparent from reference to FIG. 6 that the CCD 28 generates a digitized image of an area of contact between the tire 20 and reflective surface 26 in which the pixels of the image have a grey level value which corresponds directly to the force of engagement between the tire 20 and reflective surface 28 (and glass support plate 16) at the location corresponding to the pixel. Accordingly, the image of FIG. 6 is a spatially distributed contact force image of the inter-engagement of the tire 20 with its support surface, as well as a location image which can pinpoint, for example, the marker 38. Those skilled in the art will appreciate that the marker 38 concentrates force against the reflective surface 26 and, accordingly, results in a bright circular area of pixels having a value near the white end of the grey level spectrum as illustrated by the circular area 46. Identification of the marker 38 is thus easily achieved. Consequently, force upon the tire about the region of the marker 38 may be easily determined and movement or slip of the marker 38 while in contact with the glass plate support surface 16 and reflective surface 26 may be similarly determined. Again, the matrix of pixels generated by the CCD 28 may be thus employed to determine forces upon and movement of tire portions viewed by the CCD 28.

In accordance with the invention, it is desired to establish a particular region of interest from which force data may be obtained and analyzed, and to further establish and monitor the center of the marker 38 to determine any slip at that area when the marker 38 is in engagement with the support surface. To that end, a region of interest 54 is developed about the circular array of pixels 46 corresponding to the marker 38. It will be appreciated that the microprocessor 32 may establish a grey level threshold such that all pixels having an associated grey level value above that threshold are deemed to comprise a portion of the marker 38. It has been found that such a technique allows for ready identification of the location of the marker 38 by generation of the area 46. Having so determined the location of the approximately circular pixel array 46, the center of intensity thereof can be readily established and a region of interest 54 can be developed thereabout. In the preferred embodiment of the invention, the region of interest 54 excludes the areas 46, 48 and it is defined between outer and inner square perimeters 56, 58 as shown. The grey level of the pixels within the region of interest 54 are, accordingly, indicative of the force of the corresponding portions of the tire 20 upon the support plate 16. Such data is apparent for each image generated by the CCD 28 and microprocessor 32. On each image, the exact location of the marker 38 may also be determined by assessing the location of the circular array of bright pixels 46. Consequently, by receiving and analyzing the grey level values of the pixels within the perimeter 56 upon each image, the force upon the tire element may be readily determined by averaging the values of the grey levels of the pixels comprising the region of interest 54, while any movement or slip of that tire element can be determined by monitoring movement of the center of the region 46. It will be readily appreciated that the region of interest 54, from which force calculations are determined, excludes the marker area 38 and associated void region 40 to assure that the force calculations and determinations are not impacted by the presence of the marker 38. Additionally, the region of interest 54 is defined on each image to be centered about the region 46 which moves due to slip. Accordingly, the force and slip measurements are simultaneously taken from the same region of the tread as defined within the perimeter 56.

It should now be readily apparent that the apparatus and technique just described are capable of concurrently obtaining force and slip data from the same region of the tire under the same operating conditions, to provide accurate data from which wear propensity can be determined from the product of such data. It will further be appreciated that the force value is determined by averaging the grey levels of all of the pixels within the region of interest 54, such grey level being related to force as indicated by the associated IRL.

Figure 8:
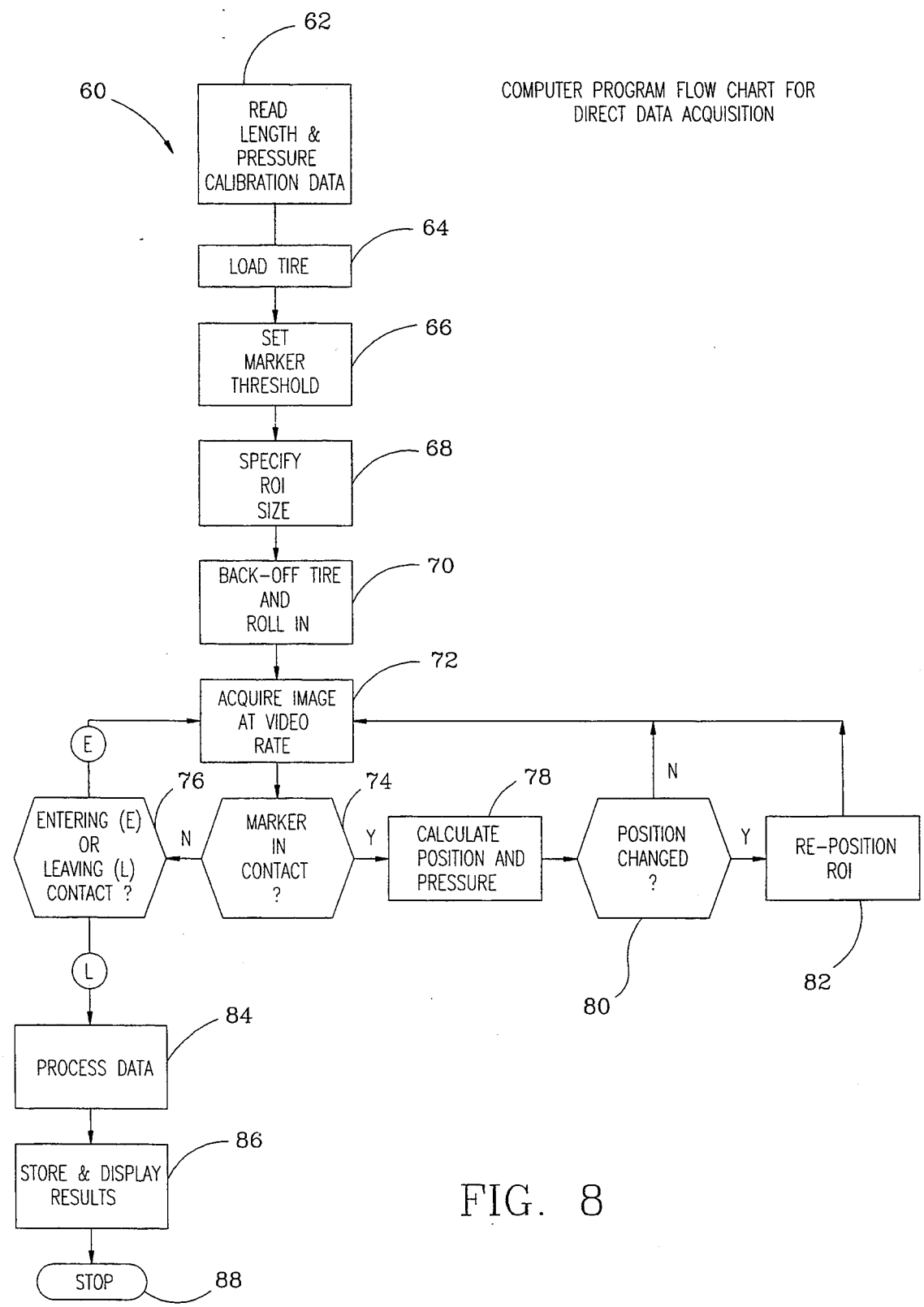
FIG. 8 is a flow chart of a process of the invention wherein data is taken directly from the tire and support surface interface.

With reference now to FIG. 8, it can be seen that the method of obtaining data directly from a tire and determining the wear propensity therefrom is designated generally by the numeral 60. As shown, a first step 62 allows for the calibration of the system 10, and particularly the establishment of relationships between pixel size and actual physical length within the field of view of the CCD 28 and a similar establishment of a relationship between grey level and force. Once pixel size and physical length and width have been correlated and a similar correlation has been made between grey level of the sensed IRL and associated force, a tire 20 is loaded onto the reflective surface 26 upon the glass support plate 16, as at step 64. At step 66 an operator establishes a threshold grey level above which the pixels of the marker 38 will typically fall. Accordingly, as the microprocessor 32 receives the digitized data of the pixels, all pixels having a grey level exceeding the threshold are deemed to comprise a portion of the marker 38 and, accordingly, will typically fall within the region 46. It has been found that the marker 38 results in sufficiently high intensity of force to allow for the selection of an appropriate threshold to readily differentiate the marker 38 from the remainder of the tire 20.

At step 68, the operator selects the physical perimeters of the region of interest 54, by establishing the lengths of the sides of the respective square inner and outer perimeters 56, 58. It will be appreciated that the steps 66, 68 are performed with the tire 20 loaded and the resultant image being demonstrated upon the screen 34. Accordingly, the establishment of the threshold and the perimeters of the region of interest 54 may be readily established.

At step 70, the tire 20 is rolled out of the field of view of the CCD 28 and then rolled back into the field of view such that the CCD 28 acquires a video image at an associated video rate at 72. A determination is made at 74 as to whether the marker 38 has made contact with the reflective surface 26. The monitoring continues through steps 76, 72, 74 until the marker 38 has entered the image and come into full contact with the reflective surface 26. At that point, step 78 determines the position of the marker 38, corresponding to the region 46, and determines the force in the region of interest 54 by averaging the grey levels of the pixels therein. A determination is made as to whether the position of the region 46 has changed from the image generated at the prior raster scan. For the first such scan, no change would have taken place and a return is made to acquire data at the next image as at 72. The process continues on each subsequent image with the determination as to the location of the marker 38 and the force imparted at the region of interest 54. On each image, the exact location of the marker 38 is determined by determining the position of the center of intensity of the associated area 46. If the position has changed, step 82 is engaged where the region of interest 54 is redefined or shifted so as to share a common center with the area 46 and marker 48. Accordingly, pressure or force determinations are always made centrally about the marker 38, but excluding the marker 38. In like manner, slip of the region of the tire bearing the marker 38 is determined by monitoring any shift in the location of the center of the region 46.

The process continues until the marker 38 is noted as leaving contact with the reflective surface 26 as at step 76. After the data acquisition process is terminated, the data is processed at 84 to determine a product of the force data and slip data obtained, such product being a direct function of the wear propensity of the tire at that area. The resultant information is stored in an appropriate memory area and displayed upon the screen 34 as evidenced at step 86. The program then concludes as at 88.

Figure 9:
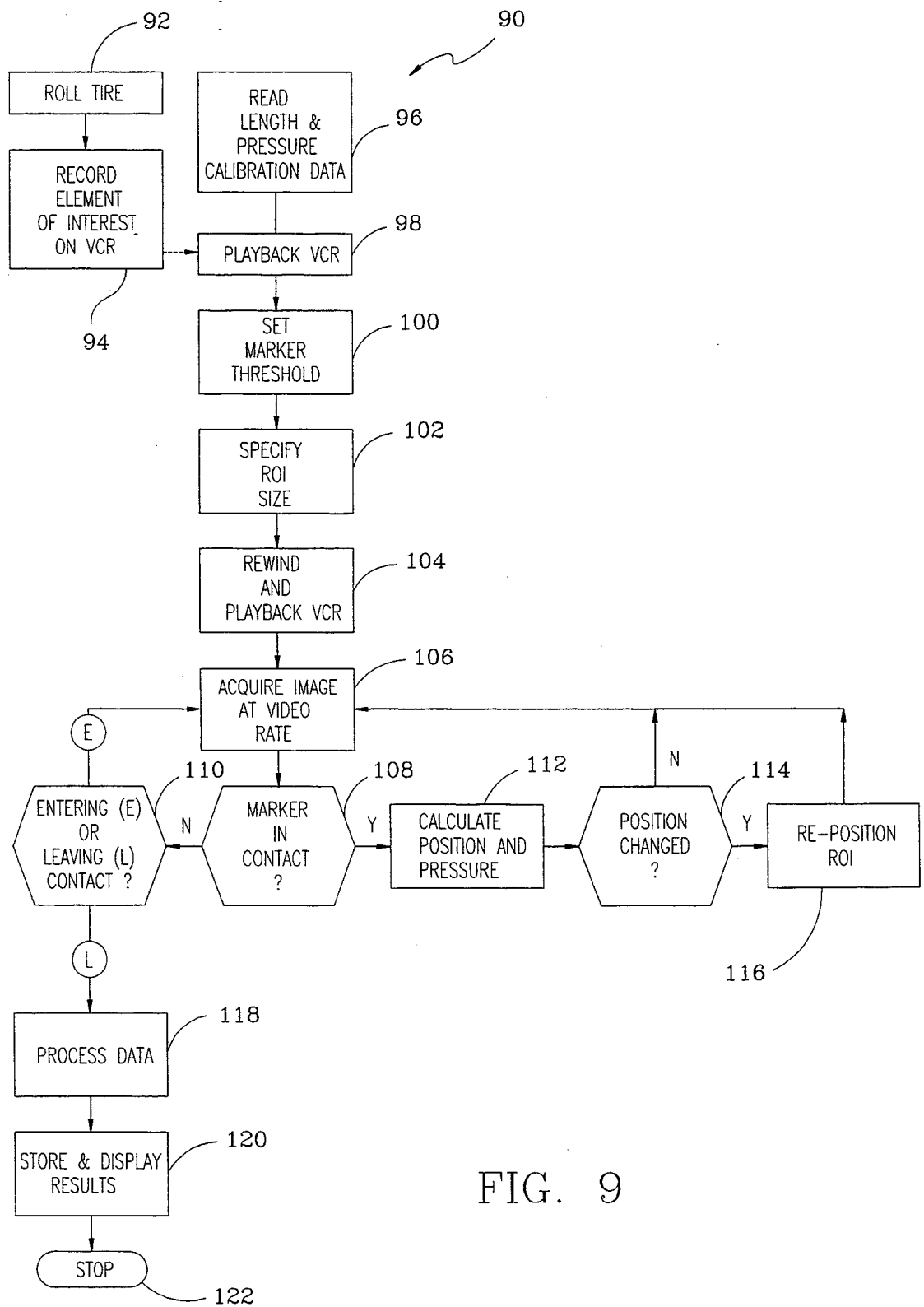
FIG. 9 is a flow chart of a process according to the invention wherein data is taken from a recorded video image of a tire at a support surface interface.

A slight variation on the theme of the process of FIG. 8 is shown in FIG. 9, designated generally by the numeral 90. Here, at step 92 the tire 90 is rolled upon the reflective surface 26 and a video record is made of the same as at 94 by the video cassette recorder 30 as shown in FIG. 1. According to the process 90, the data of force and slip is then obtained from the video image of the VCR 30, rather than directly from the tire itself.

Calibration of pixel size and grey level is achieved at 96 in a manner similar to the step 62 of FIG. 8. Once the calibration is achieved, the data from the VCR is played at 98 and viewed on the screen 44. The operator sets the threshold at 100 to differentiate the marker 38 from the remainder of the data. At 102, the boundaries and physical size of the region of interest 54 is established. Once this process is completed, the VCR is rewound and played again as at 104, with the microprocessor 32 obtaining data from the VCR at the associated video rate as at 106. The remainder of the steps designated 108-122 correspond directly with the steps 74-78 as discussed above.

The embodiment illustrated in FIG. 9 allows for the permanent maintenance of the video data of a large plurality of data points and/or tires on one video cassette, allowing for long term storage and subsequent retrieval of the same.

It should now be appreciated that an apparatus and technique have been provided to allow for a noncontacting method of obtaining data respecting frictional work and slippage at the interface of a tire and support surface, such data then being employed to determine the propensity of the tire to wear. The apparatus and techniques just described achieve the objects of the invention presented earlier herein and do so in a highly accurate and reliable manner. Specifically, the data corresponding to force and slippage are simultaneously attained under the same operating conditions and from the exact same locations on the tire to assure reliable calculations.

While in accordance with the patent statutes only the best mode and preferred embodiments of the invention have been presented and described in detail, it is to be understood that the invention is not limited thereto or thereby. Accordingly, for an appreciation of the true scope and breadth of the invention reference should be made to the following claims.

What is claimed is:

1. Apparatus for determining abrasion potential for tire treads, comprising:
    a glass plate;
    a source of illumination adjacent and illuminating said glass plate;
    first means for effecting forceful rolling engagement of a tire upon said glass plate;
    engagement of a tire upon said glass plate;
    a reflective sheet interposed between said tire and said glass plate at a contact interface therebetween;
    second means for viewing said contact interface between said tire and said glass plate and generating a digitized video image of a selected area thereof, said digitized video image comprising an array of pixels having grey level values corresponding to light intensity at said contact interface and further corresponding directly to a force of engagement of said tire upon said contact interface; and
    third means in operative communication with said second means for receiving said digitized video image, and determining therefrom a force of interengagement and an amount of slip between said selected area and said glass plate and an abrasion potential for said selected area as a function of said force and slip.

2. The apparatus according to claim 1, further comprising a marker attached to said tire and establishing said selected area.

3. The apparatus according to claim 2, wherein said second means locates said marker within said contact interface and defines said selected area as having said marker at a center thereof.

4. The apparatus according to claim 3, wherein said selected area has a center portion from which said third means determines said slip.

5. The apparatus according to claim 4, wherein said selected area has a peripheral portion surrounding, but excluding, said marker, said third means determining said force of engagement from said peripheral portion.

6. The apparatus according to claim 5, wherein said second means generates said digitized video image through repeated scan cycles, said force of interengagement and said slip being determined by said third means from data obtained from the same scan cycles.

7. The apparatus according to claim 6, wherein said marker establishes a region of disengagement between said tire and said glass plate in the form of a truncated cone.

8. The apparatus according to claim 7, wherein said marker comprises a disc adhered to a surface of the tire.

9. The apparatus according to claim 8, wherein said disc has a diameter of less than 0.10 inch, and a thickness less than 0.010 inch.

10. The apparatus according to claim 5, wherein said second means locates said marker and said third means determines said force of interengagement from gray levels of pixels within said digitized video image.

11. The apparatus according to claim 10, wherein said second means determines said marker as comprising all contiguous pixels within said digitized video image that exceed a threshold level.

12. A method for determining abrasion potential for tire treads, comprising:
 placing a marker upon a tire at an area of interest;
 rolling said tire under an applied force upon a reflective sheet interposed between said tire and illuminated glass plate;
 obtaining a digitized video image of an area of interengagement between said tire and said glass plate, said digitized video image comprising an array of pixels having grey level values corresponding to light intensity at said contact interface and further corresponding directly to a force of engagement of said tire upon said reflective sheet;
 locating said marker within said video image and defining a region of interest about said marker;
 monitoring slip of said marker in said area of interengagement;
 determining a force of interengagement between said tire and said glass plate in said region of interest; and
 assessing an abrasion potential for said tire at said region of interest as a function of said force and slip.

13. The method according to claim 12, further comprising the step of defining said marker within said video image by a first array of pixels having a grey level exceeding a threshold and surrounded by a second array of pixels having a grey level below said threshold.

14. The method according to claim 13, wherein said first array is defined as a circle and said second array is defined as a ring about said circle.

15. The method according to claim 12, wherein said region of interest about said marker excludes said marker.

16. The method according to claim 15, wherein said slip and force are continuously monitored during a period of contact between said marker and said glass plate and data respecting said slip and force are simultaneously obtained.

17. The method according to claim 16, wherein data of said digitized video image is stored and subsequently retrieved prior to said step of locating said marker and defining said region of interest.

18. The method according to claim 16, wherein said step of assessing abrasion potential comprises a step of generating a product of said slip and said force.

19. The method according to claim 16, wherein said region of interest is continuously redefined as a function of slip of said marker in said area of interengagement, a center of said marker establishing a center of said region of interest.

* * * * *